United States Patent [19]

Brockhaus et al.

[11] 4,403,098

[45] Sep. 6, 1983

[54] PROCESS FOR PRODUCING A 3,3-DIMETHYL-2-ALKOXYOXIRANE FROM A 1-ALKOXY-2-METHYLPROPENE

[75] Inventors: Rudolf Brockhaus, Marl; Hans-Jürgen Franke, Dorsten, both of Fed. Rep. of Germany

[73] Assignee: Chemische Werke Hüls Aktiengesellschaft, Marl, Fed. Rep. of Germany

[21] Appl. No.: 357,126

[22] Filed: Mar. 11, 1982

[30] Foreign Application Priority Data

Mar. 12, 1981 [DE] Fed. Rep. of Germany ....... 3109439

[51] Int. Cl.³ ............................................ C07D 301/06
[52] U.S. Cl. ..................................... 549/532; 549/512
[58] Field of Search ................................ 549/532, 512

[56] References Cited

U.S. PATENT DOCUMENTS 2,942,007  6/1960  Griffin et al. ..................... 549/532

OTHER PUBLICATIONS

Von F. Effenberger, Angew. Chem. (1969) vol. 81, No. 10, pp. 374–376.
W. Foster, Jour. Am. Chem. Soc. (1909), vol. 31, pp. 596–602.

Primary Examiner—Norma S. Milestone
Attorney, Agent, or Firm—Millen & White

[57] ABSTRACT

A process for producing a 3,3-dimethyl-2-alkoxyoxirane comprises oxidizing a 1-alkoxy-2-methylpropene with molecular oxygen in the liquid phase, at a temperature of 25°–70° C., optionally in the presence of an alkaline compound.

13 Claims, No Drawings

PROCESS FOR PRODUCING A 3,3-DIMETHYL-2-ALKOXYOXIRANE FROM A 1-ALKOXY-2-METHYLPROPENE

BACKGROUND OF THE INVENTION 3,3-Dimethyl-2-alkoxyoxiranes, which are also called 1-alkoxy-2-methylpropene oxides, and be synthesized either by reaction of the corresponding halogen compound, e.g. α-chloroisobutyraldehyde, with an alkali metal alkoxide, e.g., sodium methylate, or by oxidation of 1-alkoxy-2-methylpropenes with atomic oxygen.

Both processes are very expensive and suitable solely for the production of laboratory quantities. The manufacture of atomic oxygen, particularly, is too expensive for industrial usage.

The 3,3-dimethyl-2-alkoxyoxiranes are useful as stabilizers for chlorinated hydrocarbons. On account of their high reactivity, they are also useful as valuable synthetic intermediates. For example, by reaction with methanol, rather stable acetals are obtained which are suitable, inter alia, as solvents. Therefore, there is economic interest in manufacturing these compounds from readily accessible raw materials in an industrially simple procedure.

OBJECTS OF THE INVENTION

An object of the present invention is to provide a process for producing 3,3-dimethyl-2-alkoxyoxiranes which is commercially feasible and operationally efficient.

Upon further study of the specification and appended claims, further objects and advantages of this invention will become apparent to those skilled in the art.

SUMMARY OF THE INVENTION

These and other objects of the invention are achieved by a process for producing a 3,3-dimethyl-2-alkoxyoxirane from a 1-alkoxy-2-methylpropene, comprising contacting a 1-alkoxy-2-methylpropene with molecular oxygen, in the liquid phase, at a temperature of 25°–70° C.

DETAILED DISCUSSION

It has been discovered, surprisingly, that it is possible to oxidize a 1-alkoxy-2-methylpropene, in the liquid phase, with pure, normally gaseous molecular oxygen or with molecular oxygen diluted by inert gas, at temperatures from 25° to 70° C., preferably 30°–54° C., to obtain the corresponding 3,3-dimethyl-2-alkoxyoxirane. At lower temperatures, the reaction rate is unsatisfactory. Higher temperatures promote the formation of undesirable by-products.

The attack of molecular oxygen on the olefinic double bond with the formation of an epoxy compound is very surprising under the conditions according to the invention. Known olefin oxidation reactions in the liquid phase require, e.g., Pd complexes as the catalyst, as in the catalytic oxidation of ethylene with oxygen to produce acetaldehyde, or peroxides in the presence of molybdic acid, as in the production of epoxides, e.g., propene oxide. Therefore, the smooth reaction of isobutenyl ethers with molecular oxygen alone, according to the process of this invention, could not be expected.

This oxidative reaction of 1-alkoxy-2-methylpropenes with molecular oxygen is carried out according to the following scheme with high selectivity (yield around 75%):

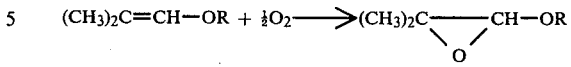

Since only the reactive group on the isobutenyl side of the enol ether is important for the oxidation reaction of this invention, any desired R group, generically denoted "alkyl," can be present on the other side of the ether molecule, as long as it is stable under the oxidation conditions. Suitable such R groups include substituted or unsubstituted alkyl, preferably lower alkyl, e.g., methyl, ethyl, n-propyl, isopropyl, n-butyl, sec.-butyl, isobutyl, tert.-butyl, especially methyl or ethyl; substituted or unsubstituted aralkyl, preferably aryl-substituted lower alkyl, e.g., benzyl, p-chlorobenzyl; substituted or unsubstituted cycloalkyl, e.g., cyclopentyl, cyclohexyl; and the like.

The 1-alkoxy-2-methylpropenes are enol ethers and can be conventionally prepared from isobutyraldehyde via the acetal by splitting off alcohol from the acetal. For experimental details, see, e.g., *Bull. Soc. Chim. Fr.*, 1007 (1965); Harrisson et al, "Compendium of Organic Synthetic Methods" (Wiley-Interscience 1971); March, "Advanced Organic Chemistry" (McGraw-Hill) 1968), H. J. Hagemeier et G. C. De Croes, "The Chemistry of Isobutyraldehyde and its derivates" Tennessee Eastman Comp. (1953) page 9; and references therein, all of which are incorporated by reference herein.

Pure, gaseous molecular oxygen or molecular oxygen diluted with one or more inert gases, e.g., air, is utilized as the molecular oxygen reactant. The reaction generally is effected under atmospheric pressure but superatmospheric pressure can also be utilized.

The molar ratio of the starting enol ether to molecular oxygen generally ranges from 10:1 to 1:1, preferably from 4:1 to 2:1. The stoichiometrical ratio is 2:1, a molar excess of oxygen is not advantageous.

The reaction can be performed under continous and/or batchwise conditions and it is advantageously conducted in a bubble column with circulating liquid through an outside situated water cooler.

Advantageously, the oxidation is effected in the presence of an alkaline compound, e.g., an alkali or alkali earth hydroxide, preferably NaOH, KOH, Ba(OH)$_2$, or mixtures thereof.

The alkaline compound is dissolved in methanol or in water.

Adding such alkaline compounds promotes the selectivity of the reaction. They are preferably employed in amounts of 50-200 ppm, although lesser amounts likewise enhance the course of the reaction. Within the aforementioned range, the progression of the reaction is optimally stabilized. The alkaline compounds stabilize the epoxide and prevent secondary reactions, e.g., the formation of dioxane derivatives or α-hydroxyacetals. They can be added in the form of an alcoholic or aqueous solution thereof.

After the reaction, the 3,3-dimethyl-2-alkoxyoxirane is separated from unreacted starting material and volatile by-products, and isolated by conventional separation methods, e.g., distillation under reduced pressure, or the like.

Without further elaboration, it is believed that one skill in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

In an oxidation apparatus comprising a circulating reactor with a reaction tube having an internal diameter of 40 mm and a height of 2,000 mm, and with a temperature-controllable product circulation, 2,660 g of 1-methoxy-2-methylpropene was contacted at 34° C. with pure, gaseous molecular oxygen. The oxygen was fed from the bottom into the reaction tube through a porous plate. The exhaust gas contained unreacted oxygen and practically no CO and $CO_2$. Small amounts of low-boiling compounds, such as acetone and methyl formate, discharged from the reactor, were condensed in a cooling system.

With progressive ether conversion, the reaction temperature was raised to 48° C. to obtain an almost complete oxygen conversion. Analyses of the reaction products were carried out with the aid of gas chromatography. The conditions and results of this Example and the following Examples, carried out in the aforedescribed apparatus, are summarized in Table I.

EXAMPLES 2–5

These Examples were conducted under the conditions set forth for Example 1, except for the changes shown in Table I. Example 2 is carried out with air instead of pure $O_2$. Example 3 is carried out with pure $O_2$ and added NaOH. Example 4 is carried out with pure $O_2$ and added KOH. Example 5 is carried out with pure $O_2$ and added NaOH, but with 1-ethoxy-2-methylpropene as the reactant. The results are shown in the Table.

scope thereof, can make various changes and modifications of the invention to adapt it to various usages and conditions.

What is claimed is:

1. A process for producing a 3,3-dimethyl-2-alkoxyoxirane from a 1-alkoxy-2-methylpropene, comprising contacting a 1-alkoxy-2-methylpropene with molecular oxygen, in the liquid phase, at a temperature of 25°–70° C.

2. A process according to claim 1, wherein said 1-alkoxy-2-methylpropene has the formula $(CH_3)_2C=CH-OR$ and said 3,3-dimethyl-2-alkoxyoxirane has the formula

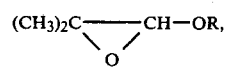

wherein R is substituted or unsubstituted alkyl, cycloalkyl or aralkyl.

3. A process according to claim 2, wherein R is $C_{1-4}$ alkyl or benzyl.

4. A process according to claim 2, wherein R is methyl or ethyl.

5. A process according to claim 1, wherein the molecular oxygen is supplied as pure, gaseous molecular oxygen.

6. A process according to claim 1, wherein the molecular oxygen is supplied diluted with an inert gas.

7. A process according to claim 6, wherein air is used as the diluted molecular oxygen source.

8. A process according to claim 1, wherein said contacting is effected at a temperature of 30°–54° C.

9. A process according to claim 1, wherein said contacting is effected under superatmospheric pressure.

10. A process according to claim 1, wherein said contacting is effected in the presence of an alkaline compound.

11. A process according to claim 10, wherein said alkali compound is sodium hydroxide, potassium hy-

OXIDATION OF 1-ALKOXY-2-METHYLPROPANE, EXPERIMENTAL DATA

| | Starting Materials and Conditions | | | | Yield Based on Converted Ether | | |
|---|---|---|---|---|---|---|---|
| Example | 1-Alkoxy-2-methylpropene | Oxidizing Gas | Alkaline Compound (ppm) | Reaction Temperature (°C.) | Ether Conversion (%) | Epoxide | (mol-%) α-Hydroxyacetal | Dioxane Derivative |
| 1 | 1-Methoxy-2-methylpropene | $O_2$ | — | 34–48 | 69 | 32.8 | 23 | 4.8 |
| 2 | 1-Methoxy-2-methylpropene | Air | — | 41–54 | 72 | 27 | 24.5 | 3.1 |
| 3 | 1-Methoxy-2-methylpropene | $O_2$ | 200 NaOH | 30–46 | 67 | 75 | 5.1 | 0.7 |
| 4 | 1-Methoxy-2-methylpropene | $O_2$ | 200 KOH | 30–45 | 76 | 69 | 5.2 | 1.5 |
| 5 | 1-Ethoxy-2-methylpropene | $O_2$ | 50 NaOH | 32–46 | 72 | 72 | 3.1 | 1.2 |

The preceding examples can be repeated with similar success by substituting the generically or specifically described reactants and/or operating conditions of this invention for those used in the preceding examples. From the foregoing description, one skilled in the art can easily ascertain the essential characteristics of this invention and, without departing from the spirit and droxide, barium hydroxide, or a mixture thereof.

12. A process according to claim 10, wherein the molar ratio of said 1-alkoxy-2-methylpropene to molecular oxygen is from 10:1 to 1:1.

13. A process according to claim 12, wherein said molar ratio is from 4:1 to 2:1.

* * * * *